US00RE42479E

(19) United States
(12) Reissued Patent
Vacanti et al.

(10) Patent Number: US RE42,479 E
(45) Date of Reissued Patent: Jun. 21, 2011

(54) ENGINEERING OF STRONG, PLIABLE TISSUES

(75) Inventors: Joseph P. Vacanti, Winchester, MA (US); Christopher K. Breuer, Bethany, CT (US); Berverly E. Chaignaud, Birmingham, AL (US); Toshiraru Shin'oka, Milford, CT (US)

(73) Assignee: Children's Medical Center Corporation, Boston, MA (US)

(21) Appl. No.: 10/782,750

(22) Filed: Feb. 19, 2004

Related U.S. Patent Documents

Reissue of:
(64) Patent No.: 6,348,069
Issued: Feb. 19, 2002
Appl. No.: 09/185,360
Filed: Nov. 3, 1998

U.S. Applications:
(62) Division of application No. 08/445,280, filed on May 19, 1995, now Pat. No. 5,855,610.

(51) Int. Cl.
*A61F 2/24* (2006.01)
(52) U.S. Cl. ..... 623/2.12; 623/2.1; 623/2.42; 424/423; 424/426; 435/395; 435/398
(58) Field of Classification Search ..... None
See application file for complete search history.

(56) References Cited

U.S. PATENT DOCUMENTS

| | | | |
|---|---|---|---|
| 1,995,970 | A | 3/1935 | Dorough |
| 2,609,347 | A | 9/1952 | Wilson |
| 2,653,917 | A | 9/1953 | Hammon |
| 2,659,935 | A | 11/1953 | Hammon |
| 2,664,366 | A | 12/1953 | Wilson |
| 2,676,945 | A | 4/1954 | Higgins |
| 2,683,136 | A | 7/1954 | Higgins |
| 2,703,316 | A | 3/1955 | Schneider |
| 2,758,987 | A | 8/1956 | Salzberg |
| 2,846,407 | A | 8/1958 | Wilson |
| 2,951,828 | A | 9/1960 | Zeile et al. |
| 3,514,791 | A | 6/1970 | Sparks |
| 3,531,561 | A | 9/1970 | Trehu |
| 3,826,241 | A | 7/1974 | Bucalo |
| 3,880,991 | A | 4/1975 | Yolles |
| 3,883,393 | A | 5/1975 | Knazek et al. |
| 3,902,497 | A | 9/1975 | Casey |
| 3,935,065 | A | 1/1976 | Doerig |
| 3,949,073 | A | 4/1976 | Daniels et al. |
| 3,960,150 | A | 6/1976 | Hussain et al. |
| 3,974,526 | A | 8/1976 | Dardik et al. |
| 3,992,725 | A | 11/1976 | Homsy |
| 3,995,444 | A | 12/1976 | Clark et al. |
| 4,026,304 | A | 5/1977 | Levy |
| 4,060,081 | A | 11/1977 | Yannas et al. |
| 4,069,307 | A | 1/1978 | Higuchi et al. |
| 4,137,921 | A | 2/1979 | Okuzumi |
| 4,141,087 | A | 2/1979 | Shalaby et al. |
| 4,144,126 | A | 3/1979 | Burbidge |
| 4,186,448 | A | 2/1980 | Brekke |
| 4,192,827 | A | 3/1980 | Mueller et al. |
| 4,205,399 | A | 6/1980 | Shalaby et al. |
| 4,228,243 | A | 10/1980 | Iizuka |
| 4,239,664 | A | 12/1980 | Teag et al. |
| 4,243,775 | A | 1/1981 | Rosensaft et al. |
| 4,277,582 | A | 7/1981 | Mueller et al. |
| 4,280,954 | A | 7/1981 | Yannas et al. |
| 4,304,591 | A | 12/1981 | Mueller et al. |
| 4,304,866 | A | 12/1981 | Green et al. |
| 4,328,204 | A | 5/1982 | Wasserman et al. |
| 4,347,847 | A | 9/1982 | Usher |
| 4,348,329 | A | 9/1982 | Chapman |
| 4,352,883 | A | 10/1982 | Lim |
| 4,356,261 | A | 10/1982 | Kuettner |
| 4,391,797 | A | 7/1983 | Folkman et al. |
| 4,416,986 | A | 11/1983 | Markus et al. |
| 4,427,808 | A | 1/1984 | Stol et al. |
| 4,431,428 | A | 2/1984 | Schmer |
| 4,438,198 | A | 3/1984 | Schmer |
| 4,439,152 | A | 3/1984 | Small |
| 4,440,921 | A | 4/1984 | Allcock et al. |
| 4,444,887 | A | 4/1984 | Hoffmann |

(Continued)

FOREIGN PATENT DOCUMENTS

| | | | |
|---|---|---|---|
| AU | 24245/88 | B | 2/1989 |

(Continued)

OTHER PUBLICATIONS

Allcock, H. R., et al., "Synthesis of Poly[(Amino Acid Alkyl Ester)Phosphazenes][1-3]", *Macromolecules,* 10(4) (Jul./Aug. 1977).

(Continued)

*Primary Examiner* — David Isabella
(74) *Attorney, Agent, or Firm* — Pabst Patent Group LLP

(57) ABSTRACT

It has been discovered that improved yields of engineered tissue following implantation, and engineered tissue having enhanced mechanical strength and flexibility or pliability, can be obtained by implantation, preferably subcutaneously, of a fibrous polymeric matrix for a period of time sufficient to obtain ingrowth of fibrous tissue and/or blood vessels, which is the removed for subsequent implantation at the site where the implant is desired. The matrix is optionally seeded prior to the first implantation, after ingrowth of the fibrous tissue, or at the time of reimplantation. The time required for fibrous ingrowth typically ranges from days to weeks. The method is particularly useful in making valves and tubular structures, especially heart valves and blood vessels.

12 Claims, No Drawings

U.S. PATENT DOCUMENTS

| | | | | |
|---|---|---|---|---|
| 4,446,229 | A | 5/1984 | Indech | |
| 4,446,234 | A | 5/1984 | Russo et al. | |
| 4,450,150 | A | 5/1984 | Sidman | |
| 4,456,687 | A | 6/1984 | Green | |
| 4,458,678 | A | 7/1984 | Yannas et al. | |
| 4,485,096 | A | 11/1984 | Bell | |
| 4,485,097 | A | 11/1984 | Bell | |
| 4,489,056 | A | 12/1984 | Himmelstein et al. | |
| 4,494,385 | A | 1/1985 | Kuraoka et al. | |
| 4,495,174 | A | 1/1985 | Allcock et al. | |
| 4,505,266 | A * | 3/1985 | Yannas et al. | 128/898 |
| 4,520,821 | A * | 6/1985 | Schmidt et al. | 606/151 |
| 4,528,265 | A | 7/1985 | Becker | |
| 4,544,516 | A | 10/1985 | Hughes et al. | |
| 4,545,082 | A | 10/1985 | Hood | |
| 4,553,272 | A | 11/1985 | Mears | |
| 4,559,298 | A | 12/1985 | Fahy | |
| 4,559,304 | A | 12/1985 | Kasai et al. | |
| 4,563,350 | A | 1/1986 | Nathan et al. | |
| 4,563,489 | A | 1/1986 | Urist | |
| 4,563,490 | A | 1/1986 | Stol et al. | |
| 4,576,608 | A | 3/1986 | Homsy | |
| 4,595,713 | A | 6/1986 | St. John | |
| 4,609,551 | A | 9/1986 | Caplan et al. | |
| 4,627,853 | A | 12/1986 | Campbell et al. | |
| 4,637,931 | A | 1/1987 | Schmitz | |
| 4,642,120 | A | 2/1987 | Nevo et al. | |
| 4,645,669 | A | 2/1987 | Reid | |
| 4,675,189 | A | 6/1987 | Kent et al. | |
| 4,675,284 | A | 6/1987 | Leevy et al. | |
| 4,681,763 | A | 7/1987 | Nathanson et al. | |
| 4,689,293 | A | 8/1987 | Goosen et al. | |
| 4,713,070 | A | 12/1987 | Mano | |
| 4,721,096 | A | 1/1988 | Naughton et al. | |
| 4,734,373 | A | 3/1988 | Bartal | |
| 4,757,017 | A | 7/1988 | Cheung | |
| 4,757,128 | A | 7/1988 | Domb et al. | |
| 4,778,749 | A | 10/1988 | Vasington et al. | |
| 4,795,459 | A * | 1/1989 | Jauregui | 623/1.41 |
| 4,801,299 | A | 1/1989 | Brendel et al. | |
| 4,846,835 | A | 7/1989 | Grande | |
| 4,853,324 | A | 8/1989 | Viles et al. | |
| 4,868,121 | A | 9/1989 | Scharp et al. | |
| 4,880,622 | A | 11/1989 | Allcock et al. | |
| 4,886,870 | A | 12/1989 | D'Amore et al. | |
| 4,888,176 | A | 12/1989 | Langer et al. | |
| 4,891,225 | A | 1/1990 | Langer et al. | |
| 4,902,289 | A * | 2/1990 | Yannas | 623/1.47 |
| 4,916,193 | A * | 4/1990 | Tang et al. | 525/413 |
| 4,946,938 | A | 8/1990 | Magill et al. | |
| 4,963,489 | A | 10/1990 | Naughton et al. | |
| 4,988,761 | A | 1/1991 | Ikada et al. | |
| 5,032,508 | A | 7/1991 | Naughton et al. | |
| 5,041,138 | A | 8/1991 | Vacanti et al. | |
| 5,078,744 | A | 1/1992 | Chvapil | |
| 5,207,705 | A * | 5/1993 | Trudell et al. | 623/1.47 |
| 5,219,361 | A | 6/1993 | von Recum et al. | |
| 5,324,519 | A | 6/1994 | Dunn et al. | |
| 5,512,600 | A | 4/1996 | Mikos et al. | |
| 5,514,378 | A * | 5/1996 | Mikos et al. | 424/425 |
| 5,709,854 | A * | 1/1998 | Griffith-Cima et al. | 424/93.7 |
| 5,720,981 | A | 2/1998 | Eisinger | |
| 5,770,193 | A * | 6/1998 | Vacanti et al. | 424/93.7 |
| 5,772,695 | A | 6/1998 | Orton | |
| 5,855,608 | A | 1/1999 | Brekke et al. | |

FOREIGN PATENT DOCUMENTS

| | | |
|---|---|---|
| DE | 28 53 614 | 7/1979 |
| DE | 35 18 150 | 10/1986 |
| EP | 0 153 896 | 9/1985 |
| EP | 0 248 246 | 6/1986 |
| EP | 0 248 247 | 6/1986 |
| EP | 0 226 061 | 6/1987 |
| EP | 0 282 746 | 9/1988 |
| EP | 0 344 924 | 5/1989 |
| EP | 0 361 957 | 9/1989 |
| EP | 0 339 607 | 11/1989 |
| JP | 62 011 459 | 1/1987 |
| JP | 63 074 498 | 4/1988 |
| JP | 63 196 273 | 8/1988 |
| JP | 63 196 595 | 8/1988 |
| WO | WO 87/06120 | 10/1987 |
| WO | WO 88/03785 | 6/1988 |
| WO | WO 89/00413 | 1/1989 |
| WO | WO 89/07944 | 9/1989 |
| WO | WO 90/12603 | 11/1990 |
| WO | WO 90/12604 | 11/1990 |
| WO | WO 91/01720 | 2/1991 |
| WO | WO 92/06702 | 4/1992 |
| WO | WO 92/07525 | 5/1992 |
| WO | WO 93/07913 | 4/1993 |
| WO | WO 93/08850 | 5/1993 |
| WO | WO 93/16687 | 9/1993 |
| WO | WO 94/21299 | 9/1994 |
| WO | WO 94/25079 | 11/1994 |

OTHER PUBLICATIONS

Allcock, H.R., et al., "Hydrolysis Pathways for Aminophosphazenes", *Inorg. Chem.* 21(1):515-521 (Jan. 1982).

Allcock, H. R., et al., "Amphilphilic Polyphosphazenes as Membrane Materials: Influence of Side Group on Radiation Cross Linking," *Biomaterials* 9(6):500-508 (Nov. 1988).

Allcock, H. R., et al., "Phosphonitrilic Compounds. IV. High Molecular Weight Poly(bis(amino)phosphazenes) and Mixed-Substituent Poly(aminophosphazenes)," *Inorg. Chem.* 11(11):2584-2590 (1972).

Allcock, H. R., et al., "Polyphosphazenes with Etheric Side Groups: Prospective Biomedical and Solid Electrolyte Polymers," *Macromolecules* 19:1508-1512 (1986).

Allcock & Kwon, "An Ionically Cross-Linkable Polyphosphazene: Poly[bis(carboxylatophenoxy)phosphazene] and Its Hydrogels and Membranes," *Macromolecules* 22:75-79 (1989).

Allcock & Kwon, "Glyceryl Phosphazenes: Synthesis, Properties, and Hydrolysis," *Macromolecules* 21(7):1980-1985 (1988).

Allcock & Scopelianos, "Synthesis of Sugar-Substituted Cyclic and Polymeric Phosphazenes and Their Oxidation, Reduction, and Acetylation Reactions," *Macromolecules* 16(5)715-719 (1983).

Atala and Casale, "Management of Primary Vesicoureteral Reflux," *Infections in Urology* pp. 39-43 (Mar./Apr. 1990).

Atala, et al., "Endoscopic Treatment of Vesicoureteral Reflux with a Chondrocyte-Alginate Suspension," *The Journal of Urology* 152:641-643 (Aug. 1994).

Atala, et al., "Endoscopic Treatment of Vesicoureteral Reflux with a Self-Detachable Balloon System," *The Journal of Urology* 148:724-728 (Aug. 1992).

Atala, et al., "Formation of Urothelial Structures in Vivo from Dissociated Cells Attached to Biodegradable Polymer Scaffolds in Vitro," *The Journal of Urology* 148:658-662 (Aug. 1992).

Atala, et al., "Implantation in Vivo and Retrieval of Artificial Structures Consisting of Rabbit and Human Urothelium and Human Bladder Muscle," *The Journal of Urology* 150:608-612 (Aug. 1993).

Atala, et al., "Injectable Alginate Seeded with Chondrocytes as a Potential Treatment for Vesicoureteral Reflux," *The Journal of Urology* 150:745-747 (Aug. 1993).

Atala, et al., "Laparoscopic Correction of Vesicoureteral Reflux," *The Journal of Urology* 150:748-751 (Aug. 1983).

Atala, et al., "Sonography with Sonicated Albumin in the Detection of Vesicoureteral Reflux," *The Journal of Urology* 150:756-758 (Aug. 1993).

Atala, "Endoscopic Treatment of Reflux with Autologous Bladder Muscle Cells," American Academy of Pediatrics Meeting held in Dalls, TX Oct. 23, 1994 (Abstract).

Atala, "Laparoscopic Treatment of Vesicoureteral Reflux," *Dia. Ped. Urol.* 14:212 (1993).

Baklund, et al. "Toward a Transplantation Therapy in Parkinson's Disease," *Annals of the N.Y. Acad. of Sci.* 495:658-673 (1987).

Bazeed, et al. "New Surgical Procedure for Management of Peyronie Disease," *Urology* 21(5), 501-504 (1983).

Bennett & Hirt, "A History of Tissue Expansion," *Dermatol. Surg. Oncol.* 19:1066-1073 (1993).

Ben-Ze'Ev, et al. "Cell-Cell and Cell-Matrix Interactions Differentially Regulate the Expression of Hepatic and Cytoskeletal Genes in Primary Cultures of Rat Hepatocytes," *Proc. Natl. Acad. Sci. USA* 85:2161-2165 (Apr. 1988).
Berrino, et al. "Surgical Correction of Breast Deformities Following Long-Lasting Complications of Polyurethane-Covered Implants," *Ann. Plast. Surg.,* 24:481 (1990).
Biers, "Organogenesis' Human Artery Equivalent May Revolutionize Vascular Grafts," *Genetic Engineering News* (Nov./Dec. 1987).
Bissell, et al. "The Role of Extracellular Matrix in Normal Liver," *Scand. J. Gastroenterol.* 23:107 (1988).
Bissell, et al., "Interactions of Rat Hepatocytes with Type IV Collagen, Fibronectin and Laminin Matrices, Distinct Matrix-Controlled Modes of Attachment and Spreading," *European Journ. of Cell Biology* 40:72-78 (1986).
"Brain Graft Seeks to Relieve Huntington Disease Patient," *New York Times* (Mar. 4, 1988).
Bissell, "Support of Cultured Hepatocytes by a Laminin-Rich Gel," *J. Clin. Invest.* 79:801-812 (1987).
Bjorklund, *Annals of the N.Y. Academy of Science* 495:676-686 (1987).
Blaivas, et al., "When Sphincter Failure is the Cause of Female Stress Incontinence," *Contemporary Urology* 5(3):33-54 (Mar. 1993).
Bohn, et al., "Adrenal Medulla Grafts Enhance Recovery of Striatal Dopaminergic Fibers," *Science* 238(4817):913-916 (Aug. 21, 1987).
Breuer, et al., "Tissue Engineering Heart Valves," American Chemical Society Spring Meeting, (Apr. 2-6, 1995).
Brown, "Fibrin-Collagen Nerve Repair Device," Inventors: Russ Griffiths, Larry Stensaas & Ken Horch, Letter dated May 10, 1988.
Burke, "The Effects of the Configuration of an Artificial Extracellular Matrix on the Development of a Functional Dermis," *The Role of Extracellular Matrix in Development* 351-355 (Alan R. Liss, Inc., NY 1984).
Cao, at al., "Bone Reconstruction with Tissue Engineered Vascularized Bone," (Abstract) Apr. 30-May 3, 1995.
Cao, et al., "The Generation of Neo-Tendon Using Synthetic Polymers seeded with Tenocytes," *Transplantation Proceedings,* 26(6):3390-3392 (1994).
Chaikin, "Tissue Engineering: Science Non-Fiction," *Medical Industry Executive* pp. 6-7 (May 1993).
Chuang, et al., "Sheath Needle for Liver Biopsy in High-Risk Patients," *RSNA* pp. 261-262 (1988).
Cilento, et al., "Phenotypic and Cytogenetic Characterization of Human Bladder Urothelia Expanded in Vitro," *Microbiology & Immunology* 152:665-670 (Aug. 1994).
Claes, et al., "Pulmonary Migration Following Periurethral Polytetrafluorethylene Injection for Urinary Incontinence," *The Journal of Urology* 142:821-822 (Sep. 1989).
Cohen, "Navigating Through Tissue Expansion Terminology," *J. Dermatol. Surg. Oncol.* 19:614-615 (1993).
Cosimi, et al., "Transplantation of Skin," *Surgical Clinics of N.A.* 58(2), 435-451 (Apr. 1978).
Collier, et al., "Norepinephrine Deficiency and Behavioral Senescence in Aged Rats: Transplanted Locus Ceruleus Neurons as an Experimental Replacement Therapy," *Annals of the New York Academy of Science* 495:396-403 (1987).
Culliton, "Gore Tex Organoids and Genetic Drugs," *Science* 246:747-749 (1989).
Da Silva, "An In Vivo Model to Quantify Motor and Sensory Peripheral Nerve Regeneration Using Bioresorbable Nerve Guide Tubes," *Brain Research,* 342:307-315 (1985).
Davis., et al., "Human Amnion Membrane Serves as a Substratum for Growing Axons in Vitro and in Vivo," *Science* 236:1106-1109 (May 29, 1987).
Del Cerro, et al., "Retinal Transplants into One Anterior Chamber of the Rat Eye," *Neuroscience* 21:(3)707-23 (Jun. 1987).
Doillon, et al., "Collagen-Based Wound Dressings: Control of the Pore Structure and Morphology," *Journal of Biomedical Materials Research,* 20:1219-1228 (1986).
Doillon, et al., "Epidermal Cells Cultured on a Collagen-Based Material," G. W. Bailey, Editor, *Proceedings of the 44th Annual Meeting of the Electron Microscopy Society of America,* (1986).
Ebata, et al. "Liver Regeneration Utilizing Isolated Hepatocytes Transplanted into the Rat Spleen," *Surg. Forum* 29: 338-340 (1978).
Elkowitz, et al., "Various Methods of Breast Reconstruction After Mastectomy: An Economic Comparison," *Plastic and Reconstructive Surgery,* 92(1):77-83 (Jul. 1993).
Erickson, "Material Help," *Scientific American* pp. 114-116 (Aug. 1992).
Ferro, et al., "Periurethral Granuloma: Unusual Complication of Teflon Periurethral Injection," *Urology* 31(5):422-423 (May 1988).
Folkman, et al., "Angiogenic Factors," *Science* 235:442-447 (Jan. 23, 1987).
Fontaine, et al., "Optimization Studies on Retroviral Mediated Gene Transfer into Rat Hepatocytes: Implications for Gene Therapy," The Society of University Surgeons, Resident's Program, Cincinnati, Ohio (Feb. 15, 1992).
Fontaine, et al., "Transplantation of Genetically Altered Hepatocytes Using Cell-Polymer Constructs," *Transplantation Proceedings,* 25:1002-1004 (Feb. 1993).
Freshney, "The Culture Environment: I. Substrate, Gas Phase, and Temperature," *Culture of Animal Cells* pp. 55-56 (Alan R. Liss, NY 1983).
Gash, "Neural Transplantation: Potential Therapy for Alzheimer's Disease," *J. Neural Trans.* [ *Suppl*] 24:301-8 (1987).
Gash, et al., "Amitiotic Neuroblastoma Cells Used for Neural Implants in Monkeys," *Science* 233(4771):1420-2 (Sep. 26, 1986).
Geiss, et al., "Multicenter Survey of Endoscopic Treatment of Vesidoureteral Reflux in Children," *Eur. Urol* 17:328-329 (1990).
Gilbert, et al., "Cell Transplantation of Genetically Altered Cells on Biodegradable Polymer Scaffolds in Syngeneic Rats," *Transplantation,* 56(2): 423-427 (Aug. 1993).
Grande, et al., "Healing of Experimentally Produced Lesions in Articular Cartilage Following Chondrocyte Transplantation," *The Anatomical Record* 218:142-148 (1987).
Grande, et al., "The Repair of Experimentally Produced Defects in Rabbit Articular Cartilage by Autologous Chondrycyte Transplantation," (May 11, 1988).
Green, "Growth of Cultured Human Epidermal Cells into Multiple Epithelia Suitable for Grafting," *Proc. Natl. Acad. Sci. USA* 76(11):5665-5668 (Nov. 1979).
Grolleman, et al., "Studies on a Bioerodible Drug Carrier System Based on Polyphosphazene," *Journal of Controlled Release* 3:143-154 (1986).
Groth, et al., "Correction of Hyperbilirubinemia in the Glucoronyltransferase-Deficient Rat by Intraportal Hepatocyte Transplantation ," *Transplant. Proc.* 9:313-316 (1977).
Hammond, et al., "Morphologic Analysis of Tissue-Expander Shape Using a Biomechanical Model," *Plastic and Reconstructive Surgery* 92(2):255-259 (Aug. 1993).
Harris, et al. "Silicone Rubber Substrata: A New Wrinkle in the Study of Cell Locomotion," *Science* 208:177-179 (1980).
Hendren & Atala, "Use of Bowel for Vaginal Reconstruction," *The Journal of Urology* 152:752-755 (Aug. 1994).
Henly, et al., "Particulate Silicone for Use in Periurethral Injections: A Study of Local Tissue Effects and a Search for Migration," *The Journal of Urology* 147(4):376A (Apr. 1992).
Henry, et al., "Nerve Regeneration Through Biodegradable Polyester Tubes," *Exp. Neurol.* 90(3): 652-676 (Dec. 1985).
Ingber, et al., "Cells as Tensecrity Structures: Architectural Regulation of Histodifferentiation by Physical Forces Transduced Over Basement Membrane," *Gene Expression During Normal and Malignant Differentiation* L.-C. Anderson, et al., editors, pp. 13-32 (Academic Press, Orlando, FL 1985).
Ingber, et al., "Endothelial Growth Factors and Extracellular Matrix Regulate DNA Synthesis Through Modulation of Cell and Nuclear Expansion," *In Vitro Cellular and Developmental Biology* 23(5):387-394 (May 1987).
Ingber, "How Does Extracellular Matrix Control Capillary Morphogenesis?" *Cell* 58:803-805 (Sep. 8, 1989).
Ingber, et al., "Control of Capillary Morphogenesis: A Molecular System of Mechanical Switches," *J. Cell Biol.,* 107:797a (1988).
Ingber, Growth Control Through Fibronectin-Dependent Modulation of Cell Shape,: (1987). *J. Cell Biol.* 105:219a (1987).

Ingber, et al., "Mechanochemical Switching Between Growth Factor-Stimulated Angiogenesis in Vitro: Role of Extracellular Matrix," *J. Cell. Biol.,* 109:317-330 (1989).
Jacksic, et al., "The Use of 'Artificial Skin' for Burns," *Ann. Rev. Med,* 38:107-116 (1987).
Jauregyu, et al., "Attachment and Long Term Survival of Adult Rat Hepatocytes in Primary Monolayer Cultures: Comparison of Different Substrata and Tissue Culture Medial Formulations," *In vitro Cellular & Development Biology,* 22(1):13-22 (Jan. 1986).
Jones, "Degradation of Artificial Tissue Substrates," *Cancer Invasion and Metastesis: Biologic and Therapeutic Aspects,* 177-185 (Raven Press, NY 1984).
Junquiera, et al., *1989 Basic Histology,* Prentice Hall, pp. 282-283 (1989).
Kehna, et al., "Diffusion of Antibiotics Across Tissue Expanders: An in Vitro Study," *Annals of Plastic Surgery* 32(4);346-349 (Apr. 1994).
Klagsburn, "Large-Scale Preparation of Chondrocytes," *Methods in Enzymology* vol. LVIII, Academic Press, New York, 1979.
Kleinman, et al., "Use of Extracellular Matrix Components and Cell Culture," *Analytical Biochemistry* 166:1-13 (1987).
Klompmaker, et al, "Porous Polymer Implants for Repair of Full-Thickness Defects of Articular Cartilage: An Experimental Study in Rabbit and Dog," *Biomaterials* 13(9):625-634 (1992).
Kolata, "Parkinson Procedure: Fervor Turns to Disillusion," *The New York Times,* (Apr. 21, 1988).
Kordower, et al., "An In Vivo and In Vitro Assessment of Differentiated Neuroblastoma Cells as a Source of Donor Tissue for Transplantation," *Annals of the New York Academy of Sciences,* 495:606-622 (new York 1987).
Kordower, et al., "Neuroblastoma Cells in Neural Transplants: A Neuroanatomical and Behavioral Analysis," *Brain Research,* 417:85-98 (1987).
Kretschmer, at al, "Autotransplantation of Pancreatic Fragments to the Portal Vein and Spleen of Total Pancreatectomized Dogs," *Ann. Surg.* 187:79-86 (Jan. 1978).
Kusano, et al., *Acta Japoni Hepato* 63:345-351 (1989).
Langer & Moses, "Biocompatible Controlled Release Polymers for Delivery of Polypeptides and Growth Factors," *Journal of Cellular Biochemistry,* 45:340-345 (1991).
Langer and Vacanti, "Tissue Engineering," *Science* 260:920-926 (May 14, 1993).
Leonard, et al., "Endoscopic Injection of Glutaraldehyde Cross-Linked Bovine Dermal Collagen for Correction of Vesidoureteral Reflux," *The Journal of Urology* 145:115-119 (Jan. 1991).
Leong, et al., "Bioerodible Polyanhydrides as Drug-Carrier Matrices. I: Characterization, Degradation, and Release Characteristics," *Journal of Biomedical Materials Research* 19:941-955 (1985).
Letourneau, "Possible Roles of Cell-to-Sutstratus Adhesion in Neuronal Morphogenesis," *Developmental Biology,* 44:77-91 (1975).
Lewin, "Cloud Over Parkinson's Therapy," *Science News,* 240: 390-392 (1988).
Lewin, "Disappointing Brain Graft Results," *Science* p. 1407 (Jun. 10, 1988).
Li, et al., Influence of a Reconstituted Basement Membrane and its Components of Casein Gene Expression and Secretion in Mouse Mammary Epithelial Cells,: *Proc. Natl. Acad. Sci. USA,* 84:136-140 (1987).
Lucas, et al, "Ectopic Induction of Cartilage and Bone by Water-Soluble Proteins from Bovine Bone Using a Ppolyanhydride Delivery Vehicle," *Journal of Biomedical Materials Research* 24(7):901-911 (1990).
Macklis, et al., "Cross-Linked Collagen Surface for Cell Culture that is Stable, Uniform, and Optically Superior to Conventional Surfaces," *In Vitro Cellular & Developmental Biology,* 21(3)(1): 189-194 (Mar. 1985).
Madison, et al., "Increased Rate of Peripheral Nerve Regeneration Using Bioresorbable Nerve Guides and Lamin-Containing Gel," *Exp. Neurol.* 88(3) 767-772 (Jun. 1985).
Madison, at al., "Nontoxic Nerve Guide Tubes Support Neovascular Growth in Transected Rat Optic Nerve," *Exp. Neurol.* 86:448-461 (1984).
Madison, rt al. "Peripheral Nerve Regeneration with Entubulation Repair: Comparison of Biodegradeable Nerve Guides Versus Polyethylene Tubes and the Effects of a Laminin-Containing Gel," *Exp. Neurol.* 95(2)387-390 (Feb. 1987).
Malizia, et al., "Migration and Granulomatous Reaction After Periurethral Injection of Polytef (Teflon)," *JAMA,* 251(24):3277-3281 (Jun. 1984).
Marciano and Gash, "Structural and Functional Relationships of Grafted Vasopressin Neurons," *Brain Res.,* 370(2):338-342 (Apr. 9, 1986).
Matas, et al., "Hepatocellular Transplantation for Metabolic Deficiencies: Decrease of Plasma Bilirubin in Gunn Rats," *Science* 192:892-894 (1976).
Matouschek, "Die Behandlung des vesikorenalen Refluxes durth Transurethrale Einspritzung von Teflonpaste," *Urologe A* 20:263-264 (1981).
Mesnil, et al., "Cell Contact but Not Junctional Communication (Dye Coupling) with Biliary Epithelial Cells is Required for Hepatocytes to Maintain Differentiated Functions," *Exper. Cell. Res.* 173:524-533 (1987).
Michapoulos & Pitot, "Primary Culture of Parenchymal Liver Cells on Collagen Membranes," *Exper. Cell. Res.* 94:70-78 (1975).
Millaruelo, "Role of Plasminogen Activator and its Inhibitors in Axonal Outgrowth and Regeneration in Vivo," *Caltech Biology,* (1987).
Minato, et al., "Transplantation of Hepatocytes for Treatment of Surgically Induced Acute Hepatic Failure in the Rat," *Eur. Surg. Res.,* 16:162-169 (1984).
Mito, et al, "Hepatocellular Transplantation," *Department of Surgery, Asahikawa Medical College* 078 4-5 Nishi-Kagura, Asahikawa, Japan.
Mittleman & Marraccini, "Pulmonary Teflon Granulomas Following Periurethral Teflon Injection for Urinary Incontinence," *Arch. Pathol. Lab. Med.* 107:611-612 (Nov. 1983).
Mooney, "Control of Hepatocyte Function Through Polymer-Substrate Modulation," *Thesis Proposal—Department of Chemical Engineering, Massuchusetts Institute of Technology* (Sep. 22, 1989).
Mooney, "Switching from Differentiation to Growth in Hepatocytes: Control by Extracellular Matrix," *J. Cell. Phys.* (151):497-505 (1992).
Mooney, et at., "Induction of Hepatocyte Differentiation by the Extracellular Matrix and an RGD-Containing Synthetic Peptide," *Mat. Res. Soc. Symp. Proc.* 252 (1992).
Mooney, et al., "Integrating Cell Transplantation and Controlled Drug Delivery Technologies to Engineer Liver Tissue," (abstract) Materials Research Society, (Apr. 17-21, 1995).
Mooney, et al., "Tissue Engineering Using Cells and Synthetic Polymers," *Transplantation Reviews* 7(3):153-162 (1993).
Mounzer, at al., "Polyglycolic Acid Mesh in Repair of Renal Injury," *Urology* 28(2):172-130 (1986).
Movitz, "Accessory Spleens and Experimental Splenosis Principles of Growth," *The Chicago Medical School Quarterly,* 26(4):183-187 (Winter-Spring 1967).
Nahi, at al., "Successful Islet Transplantation in Spontaneous Diabetes," *Surgery* 86:218-226 (1979).
Nastelin, "Pancreatic Islet Cell Transplantation: Optimization of Islet Cell Adhesion by Altering Polymer Surface Characteristics," Harvard—M.I.T. Division of Health Sciences and Technology (Feb. 1990).
Naughton, et al., "Long-Term Growth of Rat Bone Marrow Cells in a Three-Dimensional Matrix," Medical Laboratory Sciences Department, Hunter College School of Health Sciences, New York, *The Anatomical Record,* 218(1):97a (May 1987).
Naughton, at al., Granulopoiesis and Colony Stimulating Factor Production in Regenerating Liver, *Exp. Hematol.,* 10(5):451-458 (May 1982).
Naughton, et al, "Erythropoietin Production by Macrophages in the Regenerating Liver," *Journal of Surgical Oncology* 30:184-197 (1985).
Notter, et al, "Neuronal Properties of Monkey Adrenal Medulla in vitro," *Cell Tissue Res.,* 244(1):69-76 (1986).
Nyilas, et al, "Peripheral Nerve Repair with Bioresorbable Prosthese," *Trans. Am. Soc. Artif. Intern. Organs,* 29:307-313 (1983).

O'Connor, et al., "Grafting of Burns with Cultured Epithelium Prepared from Autologous Epidermal Cells," *The Lancet,* I(8210):75-78 (Jan. 1981).
O'Donell & Puri, "Treatment of Vesicoureteric Reflux by Endoscopic Injection of Teflon," *British Medical Jornal* 289:7-9 (Jul. 7, 1984).
O'C. Hamilton, "Miracle Cures May be in Your Cells," *Business Week* (Dec. 6, 1993).
Oellrich, R. G., et al. "Biliary Atresia," *Neonatal Network* pp. 25-30 (Apr. 1987).
Oliwenstein, "The Power of Plastics," *Discover* p. 18 (Dec. 1989).
Omery, "A Nursing Perspective of the Ethical Issues Surrounding Liver Transplantation," *Heart & Lung* 17(6):626-630 (Nov. 1988).
Paige, at al, "De Novo Cartilage Generation Using Calcium Alginate-Chondrocyte Constructs," Children's Hospital, Boston, MA, Plastic Surgery Research Council Meeting; N.E. Society of Plastic and Reconstructive Surgeons Meeting; and North Eastern Society of Plastic Surgeons Meeting pp. 1-34 (1993).
Pasik, *Annals of the N.Y. Academy of Science,* 495:674-675 (1987).
Patterson, et al., "Adrenal Chromaffin Cell-Derived Cholinergic Neurons for Brain Transplants," *Cattech Biology* pp. 201-202 (1987).
Perlow, M. J., "Brain Grafting as a Treatment for Parkinson's Disease," *Neurosurgery* 20(2):335-342 (1987).
Pimpl, et al., "Experimentelle Studie zur Frage der Transplantatkonditionierung and Transplantatgrofe bei heterotoper autologer Milztransplantation," *Lagenbecks Archiv* 37215-36218 (Salzburg 1984).
Pimpl, et al., "Perfusion of Autologous Splenic Grafts in Correlation with Specific Immunological Functions An Experimental Study in Pigs," *Eur. Surg. Res.* 19:53-61 (1987).
Pitman, et al., "The Use of Adhesives in Chondrocyte Transplantation Surgery: In-Vivo Studies," *Bulletin of the Hospital for Joint Diseases Orthopaedic Institute* 49(2):213-220 (1989).
Ptasinska-Urbanska, et al, "Intrascleral Introduction of Isolated Allogeneic Chondrocytes Capable of Cartilage Reformation in Rabbits; Possible Procedure in Treatment of Detachment of the Retina," *Exp. Eye. Res.,* 24(3):241-247 (1977).
Puelacher, W. C., et al., "Tissue-Engineered Growth of Cartilage: the Effect of Varying the Concentration of Chondrocytes Seeded onto Synthetic Polymer Matrices," *Int. J. Oral Maxillofac. Surg.,* 23:49-53 (1994).
Rames & Aartonson, "Migration of Polytef Paste to the Lung and Brain Following Intravesical Injection for the Correction of Reflux," *Pediatric Surgery* 6(1):239-240 (Jan. 1991).
Redmond, et al., "Fetal Neuronal Grafts in Monkeys Given Methyphenyltetrahydropyridine," *The Lancet,* pp. 1125-1127 (May 17, 1986).
Redmond, et al., "Transplants of Primate Neurons," *The Lancet* 2(8510):1046 (Nov. 1, 1986).
Reid, et al. "Long-Term Cultures of Normal Rat Hepatocytes on Liver Biomatrix," *Ann. NY Acad. Sci.* 349:70-76 (1980).
Retik, et al., "Management of Severe Hypospadias with a 2-Stage Repair," *Microbiology & Immunology* 152:749-751 (Aug. 1984).
Rhine, at al, "Polymers for Sustained Macromolecule Release: Procedures to Fabricate Reproducible Delivery Systems and Control Release Kinetics," *Journal of Pharmaceutical Sciences,* 69(3):265-269 (Mar. 1980).
Rosen, "Bioerodible Polyanhydrides for Controlled Drug Delivery," 1983 Butterworth & Co. (Publishers) Ltd.
Rosen, "Bioerodible Polymers for Controlled Release Systems," *Controlled Release Systems: Fabrication Technology,* II:83-110.
Sapozhnikova, et al., "Morphological Changes in Splenic Autografts Following Splenectomy: Experimental and Clinical Findings," *Biological Abstracts,* 86(76896) (1987).
Sasaki, "Neovascularization in the Splenic Autograft Transplanted into Rat Omentum as Studied by Scanning Electron Microscopy of Vascular Casts," *Virchows Arch.* 409:325-334 (1986).
Sawada, et al., "Effects of Extracellular Matrix Components on the Growth and Differentiation of Cultured Rat Hepatocytes," *In Vitro Cellular & Development Biology* 23(4): 267-273 (Apr. 1987).
Schmeck, "Doctors try to Capitalize on the Liver's Ability to Regenerate Itself," *The New York Times Medical Science,* (May 16, 1989).
Schubert & Baird, "Multiple Influences of a Heparin-Binding Growth Factor for Neuronal Development," *The Journal of Cell Biology* 104:635-643 (Mar. 1987).
Seckle, "Nerve Regeneration Through Synthetic Biodegradable Nerve Guides: Regulation by the Target Organ," *Plast. Reconstr. Surg.,* 74(2):173-81 (Aug. 1974).
Selden, et al., "The Pulmonary Vascular Bed as a Site for Implantation of Isolated Liver Cells in Inbred Rats," *Transplantation* 38(1):81-83 (Jul. 1984).
Shine, et al., "Cultured Peripheral Nervous System Cells Support Peripheral Nerve Regeneration Through Tubes in the Absence of Distal Nerve Stump," *Journal of Neuroscience Research* 14:393-401 (1985).
Siegel & Langer, "Controlled Release of Polypeptides and Other Macromolecules," *Pharmaceutical Research,* pp. 2-10 (1984).
Sirica, A., et al, "Use of Primary Cultures of Adult Rat Hepatocytes on Collagen Gel-Nylon Mesh to Evaluate Carcinogen-Induced Unscheduled DNA Synthesis," *Cancer Research,* 40:3259-3267 (Sep. 1980).
Sirica, et al., "Fetal Phenotypic Expression by Adult Rat Hepatocytes on Collagen Gel/Nyton Meshes," *Proc. Natl. Acad. Sci. USA,* 76(1):283-287 (Jan. 1979).
Sladek & Shoulson, "Neural Transplantation: A Call for Patience Rather Than Patients," *Science,* 240:386-388 (Jun. 10, 1988).
Sladek, "Transplantation of Fetal Dopamine Neurons in Primate Brain Reverses MPTP Induced Parkinsonism," *Progress in Brain Research* 71:309-323 (1987).
Sladek, et al, "Reversal of Parkinsonism by Fetal Nerve Cell Transplants in Primate Brain," *Annals of the New York Academy of Sciences,* 495:641-657 (1987).
Sladek, et al., "Survival and Growth of Fetal Catecholamine Neurons Transplanted Into Primate Brain," *Brain Research Bulletin,* 17:809-818 (1986).
Sommer, et al., "Hepatocellular Transplantation for Treatment of D-Galactosamine-Induced Acute Liver Failure in Rats," *Transplant. Proc.* 11(1):578-584 (Mar. 1979).
Stein, "Three Dimensional Tissue Reorganization in Hepatocyte Transplantation," American College of Surgeons, Surgical Forum, (Oct. 1991).
Stemple, *Altech Biology* (1987).
Strom, et al., "Isolation, Culture, and Transplantation of Human Hepatocytes," *JNCL,* 68(5):771-778 (May 1982).
Sudhakaran, et al., "Modulation of Protein Synthesis and Secretion by Substratum in Primary Cultures of Rat Hepatocytes," *Exper. Cell Res.* 167:505-516 (1986).
Sullivan, "Spinal Injury Research Yields a Glimmer of Hope," *The New York Times* p. C6 (Jul. 14, 1987).
Sutherland, D. E., et al., "Hepatocellular Transplantation in Acute Liver Failure," *Surgery* 82(1):124-132 (Jul. 1977).
Tachibana, "Ureteral Replacement Using Collagen Sponge Tube Grafts," *The Journal of Urology* 133(4):866-869 (Apr. 1985).
Takeda, et al,, "Hepatocyte Transplantation in Biodegradable Polymer Scaffolds Using the Dalmatian Dog Model of Hyperuricosuria," *Transplantation Proceedings* 27(1):635-636 (Feb. 1995).
Tavassoli, et al., "Studies on Regeneration of Heterotopic Splenic Autotransplants," *Blood,* 41(5):701-709 (May 1973).
Thompson, "Implantable Bioreactors: Modern Concepts of Gene Therapy," *Current Communications in Molecular Biology,* Daniel Marshak, et al., editors, pp. 143-147 (Cold Spring Harbor Laboratory, 1989).
Thompson, J. A., "Heparin-Binding Growth Factor 1 Induces the Formation of Organoid Neovascular Structures in Vivo," *Proc. Natl. Acad. Sci USA* 86:7928-27932 (Oct. 1989).
Thuroff, et al., "Cultured Rabbit Vesical Smooth Muscle Cells for Lining of Dissolvable Synthetic Prosthesis," *Urology,* 21(2):155-158 (1983).
Tomomura, et al, "The Control of DNA Synthesis in Primary Cultures of Hepatocytes From Adult and Young Rats: Interactions of Extracellular Matrix Components, Epidermal Growth Factor, and the Cell Cycle," © 1987 Alan R. Liss, Inc.
Unipoint Industries, Inc., "Polyvinyl Alcohol Foam for Surgical And Industrial Use," Product Review.

UNOS Update, "National Cooperative Transplantation Study Completed," 7(10) (Oct./Nov. 1991).
Upton, et al., Neocartilage Derived from Transplanted Perichondrium: What is it? *Plastic and Reconstructive Surgery* 68(2): 166-174 (1981).
Uyama, et al., "Delivery of Whole Liver-Equivalent Hepatocyte Mass Using Polymer Devices and Hepatotrophic Stimulation," *Transplantation* 55:932-935 (Apr. 1993).
Vacanti, et al., "Formation of New Cartilage in Vivo by Implantation of Cell-Polymer Constructs Created in Vitro,".
Vacanti, at al., "Synthetic Polymers Seeded with Chondrocytes Provide a Template for New Cartilage Formation," *Journal of the American Society of Plastic and Reconstructive Surgeons, Inc.,* 88(5):753-759 (Nov. 1991).
Vacanti, "Tissue Engineered Composites of Bone and Cartilage Using Synthetic Polymers Seeded with Two Cell Types," *39th Annual Meeting of the Orthopaedic Research Society* (Feb. 15-18, 1993).
Vacanti, "Beyond Transplantation," *Arch. Surgery* 123:545-549 (May 1988).
Vacanti, et al., "Engineered Bone from Polyglycolic Acid Polymer Scaffold and Periosteum," (abstract) Materials Research Society, (Apr. 17-21, 1985).
Vacanti, J.P., et at., Selective Cell Transplantation Using Bioabsorbable Artificial Polymers as Matrices, *Journal of Pediatric Surgery,* 23(1):3-9 (Jan. 1988).
Van Der Kwast, et al., "Establishment and Characterization of Long-Term Primary Mouse Urothelial Cell Cultures," *Urological Researach,* 17(1):290-293 (1989).
Vargo, "Infection as a Complication of Liver Transplant," *Critical Care Nurse* 9(4):52-62.
Vijg, et al., "UV-Induced DNA Excision Repair in Rat Fibroblasts During Immortalization and Terminal Differentiation in Vitro," *Exp. Cell. Res.* 167:517-530 (1986).
Vorstman, et al., "Polytetrafluoroethylene Injection for Urinary Incontinence in Children," *The Journal of Urology* 133(2):248-250 (Feb. 1985).
Vroemen, at al., "Hepatocyte Transplantation for Enzyme Deficiency Disease in Congenic Rats," *Transplantation* 42(2):130-135 (1986).
Walker, et al., "Injectable Bioglass as a Potential Substitute for Injectable Polytetrafluoroethylene," *The Journal of Urology* 148(1):645-647.
Walton, et al., "Tissue Engineering of Biomaterials for Composite Reconstruction: An Experimental Model," *Annals of Plastic Surgery* 30(2):104-110 (Feb. 1993).
Whitaker, "Scientists Growing Tissue From 'Seed'," *The Boston Globe* (Monday, Feb. 22, 1993).
Wozney, at al., "Novel Regulators of Bone Formation: Molecular Clones and Activities," *Science,* 242:1528-1534 (Dec. 16, 1988).
Yannas, at al., "Design of an Artificial Skin. I. Basic Design Principles," *Journal of Biomedical Materials Research* 14:65-81 (1980).
Yannas, et al., "Regeneration of Sciatic Nerve Across 15 mm Gap by Use of a Polymeric Template," *Polym. Sci. Technol. Iss. Adv. Biomed. Polymer* 35:109 (1987).
Yannas, "Wound Tissue Can Utilize a Polymeric Template to Synthesize a Functional Extension of Skin," *Science* 215:174-176 (1982).
Yannas, et al, "Artifical Skin: A Fifth Route to Organ Repair and Replacement," *Iss. Polym. Biomaterial,* 106:221-230 (1986).
Yannas, at al., "Polymeric Template Facilitates Regeneration of Sciatic Nerve Across 15 MM Gap," *Polymer. Material Sci. Eng.* 53:216-218 (1985).
Yannas, at al., "Suppression of In Vivo Degradability and of Immunogenicity of Collagen by Reaction with Glycosaminoglycans," *Polymer. Prepar. Am. Chem. Soc. Div. Polym. Chem.,* 16(2): 209-214 (1975).
Yannas, "What Criteria Should be Used for Designing Artifical Skin Replacement and How Well do the Current Grafting Materials Meet These Criteria?" *J. of Trauma,* 24(9):S29-S39 (1984).
Report of the International Reflux Study Committee, "Medical Versus Surgical Treatment of Primary Vesicoureteral Reflux: A Prospective International Reflux Study in Children," *The Journal of Urology* 125:277-283 (Mar. 1981).
Zund, et al., "A New Approach for a Bioprothetic-Heart Valve," The European Association for Cardio-Thoracic Surgery, (Jan. 31, 1995).

* cited by examiner

ENGINEERING OF STRONG, PLIABLE TISSUES

Matter enclosed in heavy brackets [ ] appears in the original patent but forms no part of this reissue specification; matter printed in italics indicates the additions made by reissue.

RELATED APPLICATIONS

This is a divisional of U.S. Ser. No. 08/445,280 filed May 19, 1995 now U.S. Pat. No. 5,855,610.

BACKGROUND OF THE INVENTION

This invention is generally in the field of reconstruction and augmentation of flexible, strong connective tissue such as arteries and heart valves.

Tissue engineering is a multidisciplinary science that utilizes basic principles from the life sciences and engineering sciences to create cellular constructs for transplantation. The first attempts to culture cells on a matrix for use as artificial skin, which requires formation of a thin three dimensional structure, were described by Yannas and Bell (See, for example, U.S. Pat. Nos. 4,060,081, 4,485,097 and 4,458,678). They used collagen type structures which were seeded with cells, then placed over the denuded area. A problem with the use of the collagen matrices was that the rate of degradation is not well controlled. Another problem was that cells implanted into the interior of thick pieces of the collagen matrix failed to survive.

U.S. Pat. No. 4,520,821 to Schmidt describes the use of synthetic polymeric meshes to form linings to repair defects in the urinary tract. Epithelial cells were implanted onto the synthetic matrices, which formed a new tubular lining as the matrix degraded. The matrix served a two fold purpose—to retain liquid while the cells replicated, and to hold and guide the cells as they replicated.

In European Patent Application No. 88900726.6 "Chimeric Neomorphogenesis of Organs by Controlled Cellular Implantation Using Artificial Matrices" by Children's Hospital Center Corporation and Massachusetts Institute of Technology, a method of culturing dissociated cells on biocompatible, biodegradable matrices for subsequent implantation into the body was described. This method was designed to overcome a major problem with previous attempts to culture cells to form three dimensional structures having a diameter of greater than that of skin. Vacanti and Langer recognized that there was a need to have two elements in any matrix used to form organs: adequate structure and surface area to implant a large volume of cells into the body to replace lost function and a matrix formed in a way that allowed adequate diffusion of gases and nutrients throughout the matrix as the cells attached and grew to maintain viability in the absence of vascularization. Once implanted and vascularized, the porosity required for diffusion of the nutrients and gases was no longer critical.

To overcome some of the limitations inherent in the design of the porous structures which support cell growth throughout the matrix solely by diffusion, WO 93/08850 "Prevascularized Polymeric Implants for Organ Transplantation" by Massachusetts Institute of Technology and Children's Medical Center Corporation disclosed implantation of relatively rigid, non-compressible porous matrices which are allowed to become vascularized, then seeded with cells. It was difficult to control the extent of ingrowth of fibrous tissue, however, and to obtain uniform distribution of cells throughout the matrix when they were subsequently injected into the matrix.

Many tissues have now been engineered using these methods, including connective tissue such as bone and cartilage, as well as soft tissue such as hepatocytes, intestine, endothelium, and specific structures, such as ureters. There remains a need to improve the characteristic mechanical and physical properties of the resulting tissues, which in some cases does not possess the requisite strength and pliability to perform its necessary function in vivo. Examples of particular structures include heart valves and blood vessels.

Despite major advances in its treatment over the past thirty-five years, valvular heart disease is still a major cause of morbidity and mortality in the United States. Each year 10,000 Americans die as a direct result of this problem. Valve replacement is the state-of-the art therapy for end-stage valve disease. Heart valve replacement with either nonliving xenografts or mechanical protheses is an effective therapy for valvular heart disease. However, both types of heart valve replacements have limitations, including finite durability, foreign body reaction or rejection and the inability of the nonliving structures to grow, repair and remodel, as well as the necessity of life-long anticoagulation for the mechanical prothesis. The construction of a tissue engineered living heart valve could eliminate these problems.

Atherosclerosis and cardiovascular disease are also major causes of morbidity and mortality. More than 925,000 Americans died from heart and blood vessels disease in 1992, and an estimated 468,000 coronary artery bypass surgeries were performed on 393,000 patients. This does not include bypass procedures for peripheral vascular disease. Currently, internal mammary and saphenous vein grafts are the most frequently used native grafts for coronary bypass surgery. However, with triple and quadruple bypasses and often the need for repeat bypass procedures, sufficient native vein grafts can be a problem. Surgeons must frequently look for vessels other than the internal mammary and saphenous vessels. While large diameter (0.5 mm internal diameter) vascular grafts of dacron or polytetraflorethylene (PTFE) have been successful, small caliber synthetic vascular grafts frequently do not remain patent over time. Tissue engineered blood vessels may offer a substitute for small caliber vessels for bypass surgery and replacement of diseased vessels.

It is therefore an object of the present invention to provide a method for making tissue engineered constructs which have improved mechanical strength and flexibility.

It is a further object of the present invention to provide a method and materials for making valves and vessels which can withstand repeated stress and strain.

It is another object of the present invention to provide a method improving yields of engineered tissues following implantation.

SUMMARY OF THE INVENTION

It has been discovered that improved yields of engineered tissue following implantation, and engineered tissue having enhanced mechanical strength and flexibility or pliability, can be obtained by implantation, preferably subcutaneously, of a fibrous polymeric matrix for a period of time sufficient to obtain ingrowth of fibrous tissue and/or blood vessels, which is then removed for subsequent implantation at the site where the implant is desired. The matrix is optionally seeded prior to the first implantation, after ingrowth of the fibrous tissue, or at the time of reimplantation. The time required for fibrous ingrowth typically ranges from days to weeks. The method is particularly useful in making valves and tubular structures, especially heart valves and blood vessels.

Examples demonstrate construction of blood vessels, heart valves and bone and cartilage composite structures.

DETAILED DESCRIPTION OF THE INVENTION

As described herein, structures are created by seeding of fibrous or porous polymeric matrices with dissociated cells which are useful for a variety of applications, ranging from soft tissues formed of parenchymal cells such as hepatocytes, to tissues having structural elements such as heart valves and blood vessels, to cartilage and bone. In a particular improvement over the prior art methods, the polymeric matrices are implanted into a human or animal to allow ingrowth of fibroblastic tissue, then implanted at the site where the structure is needed, either alone or seeded with [defmed] *defined* cell populations.

I. Matrix Fabrication

The synthetic matrix serves several purposes. It functions as a cell delivery system that enables the organized transplantation of large numbers of cells into the body. The matrix acts as a scaffold providing three-dimensional space for cell growth. The matrix functions as a template providing structural cues for tissue development. In the case of tissues have specific requirements for structure and mechanical strength, the polymer temporarily provides the biomechanical properties of the final construct, giving the cells time to lay down their own extracellular matrix which ultimately is responsible for the biomechanical profile of the construct. The scaffold also determines the limits of tissue growth and thereby determines the ultimate shape of tissue engineered construct. Cells implanted on a matrix proliferate only to the edges of the matrix; not beyond.

Matrix Architecture

As previously described, for a tissue to be constructed, successfully implanted, and function, the matrices must have sufficient surface area and exposure to nutrients such that cellular growth and differentiation can occur prior to the ingrowth of blood vessels following implantation. This is not a limiting feature where the matrix is implanted and ingrowth of tissue from the body occurs, prior to seeding of the matrix with dissociated cells.

The organization of the tissue may be regulated by the microstructure of the matrix. Specific pore sizes and structures may be utilized to control the pattern and extent of fibrovascular tissue ingrowth from the host, as well as the organization of the implanted cells. The surface geometry and chemistry of the matrix may be regulated to control the adhesion, organization, and function of implanted cells or host cells.

In the preferred embodiment, the matrix is formed of polymers having a fibrous structure which has sufficient interstitial spacing to allow for free diffusion of nutrients and gases to cells attached to the matrix surface. This spacing is typically in the range of 100 to 300 microns, although closer spacings can be used if the matrix is implanted, blood vessels allowed to infiltrate the matrix, then the cells are seeded into the matrix. As used herein, "fibrous" includes one or more fibers that is entwined with itself, multiple fibers in a woven or non-woven mesh, and sponge like devices.

The matrix should be a pliable, non-toxic, injectable porous template for vascular ingrowth. The pores should allow vascular ingrowth and the injection of cells in a desired density and region(s) of the matrix without damage to the cells. These are generally interconnected pores in the range of between approximately 100 and 300 microns. The matrix should be shaped to maximize surface area, to allow adequate diffusion of nutrients and growth factors to the cells and to allow the ingrowth of new blood vessels and connective tissue.

The overall, or external, matrix configuration is dependent on the tissue which is to reconstructed or augmented. The shape can also be obtained using struts, as described below, to impart resistance to mechanical forces and thereby yield the desired shape. Examples include heart valve "leaflets" and tubes.

Polymers

The term "bioerodible", or "biodegradable", as used herein refers to materials which are enzymatically or chemically degraded in vivo into simpler chemical species. Either natural or synthetic polymers can be used to form the matrix, although synthetic biodegradable polymers are preferred for reproducibility and controlled release kinetics. Synthetic polymers that can be used include bioerodible polymers such as poly(lactide) (PLA), poly(glycolic acid) (PGA), poly(lactide-co-glycolide) (PLGA), poly(caprolactone), polycarbonates, polyamides, polyanhydrides, polyamino acids, polyortho esters, polyacetals, polycyanoacrylates and degradable polyurethanes, and non-erodible polymers such as polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chloro-sulphonated polyolifins, polyethylene oxide, polyvinyl alcohol, teflon®, and nylon. Although non-degradable materials can be used to form the matrix or a portion of the matrix, they are not preferred. The preferred non-degradable material for implantation of a matrix which is prevascularized prior to implantation of dissociated cells is a polyvinyl alcohol sponge, or alkylation, and acylation derivatives thereof, including esters. A non-absorbable polyvinyl alcohol sponge is available commercially as Ivalon™, from Unipoint Industries. Methods for making this material are described in U.S. Pat. Nos. 2,609,347 to Wilson; 2,653,917 to Hammon, 2,659,935 to Hammon, 2,664,366 to Wilson, 2,664,367 to Wilson, and 2,846,407 to Wilson, the teachings of which are incorporated by reference herein. These materials are all commercially available.

Examples of natural polymers include proteins such as albumin, collagen, synthetic polyamino acids, and prolamines, and polysaccharides such as alginate, heparin, and other naturally occurring biodegradable polymers of sugar units. These are not preferred because of difficulty with quality control and lack of reproducible, defined degradation characteristics.

PLA, PGA and PLA/PGA copolymers are particularly useful for forming the biodegradable matrices. These are synthetic, biodegradable $\alpha$-hydroxy acids with a long history of medical use. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: 1,995,970 to Dorough; 2,703,316 to Schneider; 2,758,987 to Salzberg; 2,951,828 to Zeile; 2,676,945 to Higgins; and 2,683,136; 3,531,561 to Trehu.

PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", Chemistry and Industry, 905 (1970).

The erosion of the matrix is related to the molecular weights of the polymer, for example, PLA, PGA or PLA/PGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. A preferred material is poly (lactide-co-glycolide) (50:50), which degrades in about six weeks following implantation (between one and two months) and poly(glycolic acid).

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

Polymer Coatings

In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture. A preferred material for coating the polymeric matrix is polyvinyl alcohol or collagen.

Struts

In some embodiments it may be desirable to create additional structure using devices provided for support, referred to herein as "struts". These can be biodegradable or non-degradable polymers which are inserted to form a more defined shape than is obtained using the cell-matrices. An analogy can be made to a corset, with the struts acting as "stays" to push the surrounding tissue and skin up and away from the implanted cells. In a preferred embodiment, the struts are implanted prior to or at the time of implantation of the cell-matrix structure. The struts are formed of a polymeric material of the same type as can be used to form the matrix, as listed above, having sufficient strength to resist the necessary mechanical forces.

Additives to Polymer Matrices

In some embodiments it may be desirable to add bioactive molecules to the cells. A variety of bioactive molecules can be delivered using the matrices described herein. These are referred to generically herein as "factors" or "bioactive factors".

In the preferred embodiment, the bioactive factors are growth factors, angiogenic factors, compounds selectively inhibiting ingrowth of fibroblast tissue such as antiinflammatories, and compounds selectively inhibiting growth and proliferation of transformed (cancerous) cells. These factors may be utilized to control the growth and function of implanted cells, the ingrowth of blood vessels into the forming tissue, and/or the deposition and organization of fibrous tissue around the implant.

Examples of growth factors include heparin binding growth factor (hbgf), transforming growth factor alpha or beta (TGFβ), alpha fibroblastic growth factor (FGF), epidermal growth factor (TGF), vascular endothelium growth factor (VEGF), some of which are also angiogenic factors. Other factors include hormones such as insulin, glucagon, and estrogen. In some embodiments it may be desirable to incorporate factors such as nerve growth factor (NGF) or muscle morphogenic factor (MMP).

Steroidal antiinflammatories can be used to decrease inflammation to the implanted matrix, thereby decreasing the amount of fibroblast tissue growing into the matrix.

These factors are known to those skilled in the art and are available commercially or described in the literature. In vivo dosages are calculated based on in vitro release studies in cell culture; an effective dosage is that dosage which increases cell proliferation or survival as compared with controls, as described in more detail in the following examples. Preferably, the bioactive factors are incorporated to between one and 30% by weight, although the factors can be incorporated to a weight percentage between 0.01 and 95 weight percentage.

Bioactive molecules can be incorporated into the matrix and released over time by diffusion and/or degradation of the matrix, they can be suspended with the cell suspension, they can be incorporated into microspheres which are suspended with the cells or attached to or incorporated within the matrix, or some combination thereof. Microspheres would typically be formed of materials similar to those forming the matrix, selected for their release properties rather than structural properties. Release properties can also be determined by the size and physical characteristics of the microspheres.

II. Cells to Be Implanted

Cells to be implanted are dissociated using standard techniques such as digestion with a collagenase, trypsin or other protease solution. Preferred cell types are mesenchymal cells, especially smooth or skeletal muscle cells, myocytes (muscle stem cells), fibroblasts, chondrocytes, adipocytes, fibromyoblasts, and ectodermal cells, including ductile and skin cells, hepatocytes, Islet cells, cells present in the intestine, and other parenchymal cells, osteoblasts and other cells forming bone or cartilage. In some cases it may also be desirable to include nerve cells. Cells can be normal or genetically engineered to provide additional or normal function. Methods for genetically engineering cells with retroviral vectors, polyethylene glycol, or other methods known to those skilled in the art can be used.

Cells are preferably autologous cells, obtained by biopsy and expanded in culture, although cells from close relatives or other donors of the same species may be used with appropriate immunosuppression. Immunologically inert cells, such as embryonic or fetal cells, stem cells, and cells genetically engineered to avoid the need for immunosuppression can also be used. Methods and drugs for immunosuppression are known to those skilled in the art of transplantation. A preferred compound is cyclosporin using the recommended dosages.

In the preferred embodiment, cells are obtained by biopsy and expanded in culture for subsequent implantation. Cells can be easily obtained through a biopsy anywhere in the body, for example, skeletal muscle biopsies can be obtained easily from the arm, forearm, or lower extremities, and smooth muscle can be obtained from the area adjacent to the subcutaneous tissue throughout the body. To obtain either type of muscle, the area to be biopsied can be locally anesthetized with a small amount of lidocaine injected subcutaneously. Alternatively, a small patch of lidocaine jelly can be applied over the area to be biopsied and left in place for a period of 5 to 20 minutes, prior to obtaining biopsy specimen. The biopsy can be effortlessly obtained with the use of a biopsy needle, a rapid action needle which makes the procedure extremely simple and almost painless. With the addition of the anesthetic agent, the procedure would be entirely painless. This small biopsy core of either skeletal or smooth muscle can then be transferred to media consisting of phosphate buffered saline. The biopsy specimen is then transferred to the lab where the muscle can be grown utilizing the explant technique, wherein the muscle is divided into very pieces which are adhered to culture plate, and serum containing media is added. Alternatively, the muscle biopsy can be enzymatically digested with agents such as trypsin and the cells dispersed in a culture plate with any of the routinely used medias. After cell expansion within the culture plate, the cells can be easily passaged utilizing the usual technique until an adequate number of cells is achieved.

III. Methods for Implantation

Unlike other prior art methods for making implantable matrices, the present method uses the recipient or an animal as the initial bioreactor to form a fibrous tissue-polymeric construct which optionally can be seeded with other cells and implanted. The matrix becomes infiltrated with fibrous tissue and/or blood vessels over a period ranging from between one day and a few weeks, most preferably one and two weeks. The matrix is then removed and implanted at the site where it is needed.

In one embodiment, the matrix is formed of polymer fibers having a particular desired shape, that is implanted subcutaneously. The implant is retrieved surgically, then one or more defined cell types distributed onto and into the fibers. In a second embodiment, the matrix is seeded with cells of a defined type, implanted until fibrous tissue has grown into the matrix, then the matrix removed, optionally cultured further in vitro, then reimplanted at a desired site.

The resulting structures are dictated by the matrix construction, including architecture, porosity (% void volume and pore diameter), polymer nature including composition, crystallinity, molecular weight, and degradability, hydrophobicity, and the inclusion of other biologically active molecules.

This methodology is particularly well suited for the construction of valves and tubular structures. Examples of valves are heart valves and valves of the type used for ventricular shunts for treatment of hydrocephaly. A similar structure could be used for an ascites shunt in the abdomen where needed due to liver disease or in the case of a lymphatic obstructive disease. Examples of tubular structures include blood vessels, intestine, ureters, and fallopian tubes.

The structures are formed at a site other than where they are ultimately required. This is particularly important in the case of tubular structures and valves, where integrity to fluid is essential, and where the structure is subjected to repeated stress and strain.

The present invention will be further understood by reference to the following non-limiting examples.

EXAMPLE 1

Tissue Engineering of Heart Valves

Valvular heart disease is a significant cause of morbidity and mortality. Construction of a tissue engineered valve using living autologous cells offers advantages over currently used mechanical or glutaraldehyde fixed xenograft valves.

Methods and Materials

A tissue engineered valve was constructed by seeding a synthetic polyglycolic acid (PGA) fiber based matrix with dissociated fibroblasts and endothelial cells harvested from a donor sheep heart valve. The cells were grown to confluence and split several times to increase the cell number. A mixed cell population including myofibroblasts and endothelial cells was obtained. The endothelial cells were labeled with an Ac-Dil-LDL fluorescent antibody obtained from a commercial source and sorted in a cell-sorting machine to yield a nearly pure endothelial cell population (LDL+) and a mixed cell population containing myofibroblasts and endothelial cells (LDL−). A PGA mesh (density 76.9 mg/ml and thickness 0.68 mm) was seeded with the mixed cell population and grown in culture. When the myofibroblasts reached confluence, endothelial cells were seeded onto the surface of the fibroblast/mesh constructs and grown into a single monolayer.

Immunohistochemical evaluation of constructs with antibodies against factor VIII, a specific marker for endothelial cells, revealed that tissue engineered valves histologically resemble native valve tissue. The effects of physiological flow on elastin and collagen production within the ECM were examined in a bioreactor and implanted in a sheep to determine if the constructs had the required pliability and mechanical strength for use in patients.

EXAMPLE 2

Tissue Engineering of Vascular Structures

Vascular smooth muscle tubular structures using a biodegradable polyglycolic acid polymer scaffold have been developed. The technique involves the isolation and culture of vascular smooth muscle cells, the reconstruction of a vascular wall using biodegradable polymer, and formation of the neotissue tubes in vitro. The feasibility of engineering vascular structures by coculturing endothelial cells with fibroblasts and smooth muscle cells on a synthetic biodegradable matrix in order to create tubular constructs which histologically resemble native vascular structures was also demonstrated.

Methods

In a first set of studies, bovine and ovine endothelial cells, smooth muscle cells, and fibroblasts were isolated using a combination of standard techniques including collagenase digestion and explantation. These cells were then expanded in tissue culture. All cells were grown in Delbecco's modified Eagle's media supplemented with 10% fetal bovine serum, 1% antibiotic solution, and basic fibroblast growth factor. Mixed colonies were purified using dilutional cloning. Thirty (N=30) two by two centimeter polyglycolic acid (PGA) fiber meshes (thickness=0.68 mm, density=76.9 mg/cc) were then serially seeded with $5\times10^5$ fibroblasts and smooth muscle cells and placed in culture. Five (N=5) 85% PGA, 15% polylatic acid tubular constructs (length=2 cm, diameter=0.8 cm) were seeded in a similar fashion. After the fibroblasts and smooth muscle cell constructs had grown to confluence (mean time 3 weeks), $1\times10^6$ endothelial cells were seeded onto them and they were placed in culture for one week. These vascular constructs were then fixed in a paraffin, sectioned and analyzed using immunohistochemical staining for factor VIII (specific for endothelial cells) and desmin (specific for muscle cells).

In a second set of studies, smooth muscle cells were obtained by harvesting the media from the artery of a lamb using standard explant techniques. Cells were expanded in culture through repeated passages and then seeded on the biodegradable polymer scaffold at a density of $1\times10^6$ cells per $cm^2$ of polymer. The cell-polymer constructs were formed into tubes with internal diameters ranging from 2 mm to 5 mm and maintained in vitro for 6 to 8 weeks.

Results

Microscopic examination of all constructs in the first study (N=30/N=5) revealed that both types of constructs had achieved the proper histological architecture and resembled native vessels after one week. Immunohistochemical staining confirmed that endothelially lined smooth muscle/fibroblast tubes had been created. The extracellular matrices (ECM) of the vascular constructs were examined in order to determine the composition of elastin and collagen types I and III, the ECM molecules which determine the physical characteristics of native vascular tissues.

The results of the second study show that vascular smooth muscle tubes which retain their structure can be successfully formed using a polyglycolic acid polymer scaffold. The biodegradable polymer was absorbed over time, leaving a neotissue vascular smooth muscle tube.

EXAMPLE 3

Engineered bone from PGA Polymer Scaffold and Periosteum

The ability to create bone from periosteum and biodegradable polymer may have significant utility in reconstructive orthopedic and plastic surgery. Polyglycolic acid (PGA) is a preferred material for forming a biodegradable matrix which can be configured to a desirable shape and structure. This study was conducted to determine whether new bone constructs can be formed from periosteum or periosteal cells placed onto PGA polymer.

Materials and Methods

Bovine periosteum, harvested from fresh calf limbs, was placed either directly onto PGA polymer (1×1 cm) or onto tissue culture dishes for periosteal cell isolation. The periosteum/PGA construct was cultured for one week in MEM 199 culture media with antibiotics and ascorbic acid, then implanted into the dorsal subcutaneous space of nude mice. Periosteal cell, cultured from pieces of periosteum for two weeks, were isolated into cell suspension and seeded (approximately 1 to $3\times10^7$ cells) onto PGA polymer (1 ×1 cm); after one week in culture, the periosteal cell seeded polymer was implanted into the subcutaneous space of nude mice. Specimens, harvested at 4, 8, and 14 week intervals, were evaluated grossly and histologically.

Results

The periosteum/PGA constructs showed an organized cartilage matrix with early evidence of bone formation at four weeks, a mixture of bone and cartilage at 8 weeks, and a complete bone matrix at 14 weeks. Constructs created from periosteal cells seeded onto polymer showed presence of disorganized cartilage at 4 and 8 weeks, and a mixture of bone and cartilage at 14 weeks. Periosteum placed directly onto polymer will form an organized cartilage and bone matrix earlier than constructs formed from periosteal cell seeded polymer. This data indicates that PGA is an effective scaffold for periosteal cell attachment and migration to produce bone, which may offer new approaches to reconstructive surgery.

EXAMPLE 4

Bone Reconstruction with Tissue Engineered Vascularized Bone

The aim of this study was to determine if new vascularized bone could be engineered by transplantation of osteoblast around existing vascular pedicle using biodegradable polymers as cell delivery devices, to be used to reconstruct weight bearing bony defects.

Methods

Osteoblast and chondryocytes were isolated from calf periosteum and articular cartilage, cultured in vitro for three weeks, then seeded onto a 1×1 cm non-woven polyglycolic acid (PGA) mesh. After maintenance in vitro for one week, cell-polymer constructs were wrapped around saphenous vessels, and implanted into athymic rats for 8 weeks. The implants showed gross and histological evidence of vascularized bone or cartilage. At this time, bilateral 0.8 cm femoral shaft defect were created in the same rat, and fixed in position with a 3 cm craniofacial titanium miniplate. The new engineered bone/cartilage construct was then transferred to the femoral defect on its bilateral vascular pedicle. A total of 30 femoral defects were repaired in three groups of animals (each group composed of five animals with defects). Animals in Group 1 received implants composed of vascularized bone constructs, animals in Group 2 with vascular cartilage constructs, and Group 3 animals with blank polymer only.

At six months after surgery, the animals were studied radiographically for evidence of new bone formation at the site of the defect. Euthanasia was then performed by anesthetic overdose and each experimented femur was removed. Gross appearance was recorded and histological studies performed using hematoxylin and eosin (H & E) staining.

Results

Group 1 defect showed evidence of new bone formation around the defect. Neither Group 2 nor Group 3 defect showed any radiographic evidence of healing or bone formation. Grossly, Group 1 animals developed exuberant bony callus formation and healing of the defect. The animals in Group 2 showed filling of the bony defect with cartilaginous tissue, whereas all of the animals in Group 3 either developed a fibrous non-union or simple separation of both bony fragments with soft tissue invasion of the defect. The histological studies showed new bone formation in all Group 1 animals, new cartilage formation in all Group 2 animals, and fibrous tissue invasion in all Group 3 animals.

Conclusion

In conclusion, it was possible to engineer vascularized bone and cartilage grafts, which could be used to repair bone defects in the rat femur. Engineered tissue maintained the characteristics of the tissues form which the cells were originally isolated.

EXAMPLE 5

Engineering of Composite Bone and Cartilage

The ability to construct a composite structure of bone and cartilage offers a significant modality in reconstructive plastic and orthopedic surgery. The following study was conducted to engineer a bone and cartilage composite structure using periosteum, chondrocytes and biodegradable polymer and to direct bone and cartilage formation by selectively placing periosteum and chondrocytes onto the polymer scaffold.

Methods and materials

Bovine periosteum and cartilage were harvested from newborn calf limbs. Periosteum (1.5×2.0 cm) was wrapped around a polyglycolic acid/poly L-lactic acid co-polymer tube (3 cm in length, 3 mm in diameter), leaving the ends exposed. The cartilage pieces were enzymatically digested with collagenase, and chondrocytes ($2\times10^7$ cells) were seeded onto each end of the exposed polymer. The composite construct was cultured for seven days in Medium 199 with antibiotics, fetal bovine serum, and ascorbic acid at 37° C. with 5% $CO_2$. Eight constructs were then implanted into the dorsal subcutaneous space of eight nude mice. After 8 to 14 weeks in vivo, the implants were harvested and evaluated grossly and histologically.

Results

All implants formed into cylindrical shapes, flattened at the ends. The central portion of the implant formed into a bony matrix and the ends of the specimens formed into cartilage, approximately where the periosteum and chondrocytes were placed. Histological sections showed an organized matrix of bone and cartilage with a distinct transition between bone and cartilage.

Conclusions

The results show that periosteum and chondrocytes placed onto a biodegradable polymer will form into a composite tissue of bone and cartilage. Moreoever, bone and cartilage composite formation with selective placement of periosteum and chondrocytes on a biodegradable polymer scaffold was shown.

EXAMPLE 6

Implantation of Matrix for Ingrowth of Fibrous Tissue to Increase Mechanical Properties and Cell Survival The following study was conducted to increase the mechanical strength and pliability of the heart valve leaflets or other engineered tissues such as those for use as blood vessels.

Methods

A PGA mesh as described in Example 1 or 2 was implanted subcutaneously in an animal, then removed after a period of one to two weeks. Fibroblasts migrated into the polymeric mesh while it was implanted. The implant was then seeded with other cells such as chondrocytes or endothelial cells and cultured in vitro for an additional period of time.

Results

The resulting implant was shown to have greater mechanical strength and pliability than implants formed solely by seeding of dissociated cells.

Modifications and variations of the method and compositions described herein will be obvious to those skilled in the art from the foregoing detailed description. Such modifications and variations are intended to come within the scope of the appended claims.

We claim:

1. A method for making a cell-matrix construct [for use as] *in the shape of* a heart valve [or blood vessel] *or heart valve leaflet* comprising implanting into an animal [at a first site] *a cell-matrix construct comprising*

(*a*) a fibrous matrix [formed] *in the shape of a heart valve or heart value leaflet, wherein the matrix consists* of a synthetic*, biocompatible, chemically* biodegradable polymer*, and*

(*b*) [having seeded therein a mixture of] cells selected from the group [selected from] *consisting of* endothelial cells, myofibroblasts, skeletal muscle cells, vascular smooth muscle cells, myocytes, fibromyoblasts, and ectodermal cells, *seeded thereon,* wherein the *synthetic chemically biodegradable polymer provides the biochemical properties of a heart valve or leaflet until the seeded cells can lay down their own extracellular matrix, and*

[matrix is formed of a biocompatible, biodegradable polymer, and implanting into an animal or human the matrix at a site where the resulting cell-construct is needed] *the matrix is formed so that the cells attach to and proliferate on it to the edges of the matrix.*

2. The method of claim 1 [further comprising seeding] *wherein* the matrix *is seeded* with dissociated [parenchymal or] connective tissue cells.

3. The method of claim 1 wherein the matrix is first cultured at a first site in a patient prior to being [implanted at] *transplanted to* a second site.

4. The method of claim 1 wherein the matrix is *in the form of* a heart valve [and is implanted in the heart] *leaflet*.

5. The method of claim 1 wherein the cell-matrix construct is seeded with vascular smooth muscle cells and endothelial cells [is] *and* implanted to form a *heart* valve.

[6. The method of claim 5 wherein the valve is a heart valve.]

[7. The method of claim 1 wherein the cell-matrix construct is seeded with endothelial cells and implanted to form a blood vessel.]

*8. The method of claim 1 wherein the cell-matrix construct is formed of a potymer selected from the group consisting of poly(lactide) (PLA), poly(glycolic acid) (PGA), poly(lactide-co-glycolide) (PLGA), poly(caprolactone), polyanhydrides, polyamino acids, and polyortho esters.*

*9. The method of claim 1 wherein the cell-matrix construct contains interconnected pores in the range of between approximately 100 and 300 microns.*

*10. The method of claim 1 wherein the cell-matrix construct includes growth factors.*

*11. The method of claim 10 wherein the growth factors are selected from the group consistin of heparin binding growth factor (hbgf), transforming growth factor alpha or beta (TGFβ), alpha fibroblastic growt.h...factor (FGF),.epidermal growth factor (TGF), vascular endothelium growth factor (VEGF), insulin, glucagon, estrogen, nerve growth factor (NGF) and muscle morphogenic factor (MMP).*

*12. The method of claim 1 wherein the cell-matrix further comprises bioactive factors incorporated to between one and 30% by weight.*

*13. The method of claim 1 wherein the cell-matrix is first cultured in a bioreactor to form a fibrous tissue-polymeric construct before implantation.*

*14. The method of claim 13 wherein the bioreactor is an animal.*

* * * * *